US008888681B2

(12) United States Patent
Weisman

(10) Patent No.: US 8,888,681 B2
(45) Date of Patent: Nov. 18, 2014

(54) METHOD AND APPARATUS FOR BILIARY ACCESS AND STONE RETRIEVAL

(71) Applicant: Boston Scientific Scimed, Inc., Maple Grove, MN (US)

(72) Inventor: Michal Weisman, Somerville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 10 days.

(21) Appl. No.: 13/764,085

(22) Filed: Feb. 11, 2013

(65) Prior Publication Data

US 2013/0144119 A1 Jun. 6, 2013

Related U.S. Application Data

(63) Continuation of application No. 11/962,211, filed on Dec. 21, 2007, now Pat. No. 8,372,000.

(60) Provisional application No. 60/883,287, filed on Jan. 3, 2007.

(51) Int. Cl.
| | | |
|---|---|---|
| A61B 1/00 | (2006.01) | |
| A61B 17/221 | (2006.01) | |
| A61B 1/06 | (2006.01) | |
| A61B 1/018 | (2006.01) | |
| A61B 19/00 | (2006.01) | |

(52) U.S. Cl.
CPC ....... *A61B 17/221* (2013.01); *A61B 2019/5217* (2013.01); *A61B 1/0661* (2013.01); *A61B 1/018* (2013.01)
USPC ............ 600/104; 600/106; 600/107; 600/153

(58) Field of Classification Search
CPC ............ A61B 1/0008; A61B 1/00085; A61B 1/00154
USPC ................. 600/104, 106–107, 121–125, 153; 606/106–108, 113–114
See application file for complete search history.

(56) References Cited

U.S. PATENT DOCUMENTS

| | | | |
|---|---|---|---|
| 561,059 | A | 5/1896 | Mitchell et al. |
| 1,204,053 | A | 11/1916 | Moore |
| 1,213,001 | A | 1/1917 | Philips |
| 1,901,731 | A | 3/1933 | Buerger |
| 2,623,520 | A | 12/1952 | Bamford, Jr. et al. |
| 3,015,869 | A | 1/1962 | Rapata |

(Continued)

FOREIGN PATENT DOCUMENTS

| | | |
|---|---|---|
| DE | 4115007 A1 | 11/1992 |
| EP | 0328760 A2 | 8/1989 |

(Continued)

OTHER PUBLICATIONS

Knecht, Gregory I., M.D. et al., "Double-Channel Fistulotome for Endoscopic Drainage of Pancreatic Pseudocyst", Gastrointestinal Endoscopy, vol. 37, No. 3, May/Jun. 1991, pp. 356-357.

(Continued)

*Primary Examiner* — Matthew J Kasztejna
(74) *Attorney, Agent, or Firm* — Seager, Tufte & Wickhem, LLC

(57) ABSTRACT

Endoscopes, endoscopic instruments, and methods for making and using the same. An illustrative endoscopic instrument includes a catheter that can extend through the working channel of an endoscope. The catheter may include an end effector passing region.

18 Claims, 6 Drawing Sheets

(56) References Cited

U.S. PATENT DOCUMENTS

| | | |
|---|---|---|
| 3,536,281 A | 10/1970 | Meehan et al. |
| 3,602,228 A | 8/1971 | Cowley |
| 3,677,243 A | 7/1972 | Nerz |
| 4,178,920 A | 12/1979 | Cawood, Jr. et al. |
| 4,306,562 A | 12/1981 | Osborne |
| 4,326,516 A | 4/1982 | Schultz et al. |
| 4,345,606 A | 8/1982 | Littleford |
| 4,411,654 A | 10/1983 | Boarini et al. |
| 4,412,832 A | 11/1983 | Kling et al. |
| 4,474,174 A | 10/1984 | Petruzzi |
| RE31,855 E | 3/1985 | Osborne |
| 4,509,944 A | 4/1985 | King et al. |
| 4,609,370 A | 9/1986 | Morrison |
| 4,611,594 A | 9/1986 | Grayhack et al. |
| 4,687,470 A | 8/1987 | Okada |
| 4,696,668 A | 9/1987 | Wilcox |
| 4,700,694 A | 10/1987 | Shishido |
| 4,715,360 A | 12/1987 | Akui et al. |
| 4,723,942 A | 2/1988 | Scott |
| 4,738,666 A | 4/1988 | Fuqua |
| 4,748,982 A | 6/1988 | Horzewski et al. |
| 4,762,129 A | 8/1988 | Bonzel |
| 4,771,777 A | 9/1988 | Horzeeski et al. |
| 4,781,677 A | 11/1988 | Wilcox |
| 4,787,884 A | 11/1988 | Goldberg |
| D301,365 S | 5/1989 | Gette |
| 4,835,824 A | 6/1989 | Durham et al. |
| 4,844,092 A | 7/1989 | Rydell et al. |
| 4,858,810 A | 8/1989 | Intlekofer et al. |
| 4,867,605 A | 9/1989 | Myers et al. |
| 4,900,184 A | 2/1990 | Cleveland |
| 4,905,667 A | 3/1990 | Foerster et al. |
| 4,917,103 A | 4/1990 | Gambale et al. |
| 4,927,418 A | 5/1990 | Dake et al. |
| 4,928,669 A | 5/1990 | Sullivan |
| 4,928,693 A | 5/1990 | Goodin et al. |
| 4,932,413 A | 6/1990 | Shockey et al. |
| 4,940,062 A | 7/1990 | Hampton et al. |
| 4,946,443 A | 8/1990 | Hauser et al. |
| 4,973,329 A | 11/1990 | Park et al. |
| 4,983,168 A | 1/1991 | Moorehead |
| 4,988,356 A | 1/1991 | Crittenden et al. |
| 4,995,872 A | 2/1991 | Ferrara |
| 4,997,421 A | 3/1991 | Palsrok et al. |
| 5,026,366 A | 6/1991 | Leckrone |
| 5,034,001 A | 7/1991 | Garrison et al. |
| 5,040,548 A | 8/1991 | Yock |
| 5,061,273 A | 10/1991 | Yock |
| 5,064,414 A | 11/1991 | Revane |
| 5,125,915 A | 6/1992 | Berry et al. |
| 5,127,393 A | 7/1992 | McFarlin et al. |
| 5,135,535 A | 8/1992 | Kramer |
| 5,137,288 A | 8/1992 | Starkey et al. |
| 5,137,517 A | 8/1992 | Loney et al. |
| 5,139,032 A | 8/1992 | Jahrmarkt et al. |
| 5,147,377 A | 9/1992 | Sahota |
| 5,154,725 A | 10/1992 | Leopold |
| 5,158,545 A | 10/1992 | Trudell et al. |
| 5,160,323 A | 11/1992 | Andrew |
| 5,161,534 A | 11/1992 | Berthiaume |
| 5,163,941 A | 11/1992 | Garth et al. |
| 5,167,634 A | 12/1992 | Corrigan, Jr. et al. |
| 5,171,222 A | 12/1992 | Euteneuer et al. |
| 5,180,367 A | 1/1993 | Kontos et al. |
| 5,191,888 A | 3/1993 | Palmer et al. |
| 5,195,978 A | 3/1993 | Schiffer |
| 5,205,822 A | 4/1993 | Johnson et al. |
| 5,219,332 A | 6/1993 | Nelson et al. |
| 5,219,335 A | 6/1993 | Willard et al. |
| 5,232,445 A | 8/1993 | Bonzel |
| 5,248,306 A | 9/1993 | Clark et al. |
| 5,250,033 A | 10/1993 | Evans et al. |
| 5,259,366 A | 11/1993 | Reydel et al. |
| 5,263,932 A | 11/1993 | Jang |
| 5,267,958 A | 12/1993 | Buchbinder et al. |
| 5,279,562 A | 1/1994 | Sirhan et al. |
| 5,281,203 A | 1/1994 | Ressemann |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock |
| 5,306,247 A | 4/1994 | Pfenninger |
| 5,308,318 A | 5/1994 | Plassche, Jr. |
| 5,314,408 A | 5/1994 | Salmon et al. |
| 5,320,602 A | 6/1994 | Karpiel |
| 5,324,259 A | 6/1994 | Taylor et al. |
| 5,324,269 A | 6/1994 | Miraki |
| 5,328,472 A | 7/1994 | Steinke et al. |
| 5,334,143 A | 8/1994 | Carroll |
| 5,334,147 A | 8/1994 | Johnson |
| 5,334,187 A | 8/1994 | Fischell et al. |
| 5,336,184 A | 8/1994 | Teirstein |
| 5,342,297 A | 8/1994 | Jang |
| 5,350,395 A | 9/1994 | Yock |
| 5,352,215 A | 10/1994 | Thome et al. |
| 5,357,978 A | 10/1994 | Turk |
| 5,364,355 A | 11/1994 | Alden et al. |
| 5,364,376 A | 11/1994 | Horzewski et al. |
| 5,368,567 A | 11/1994 | Lee |
| 5,370,623 A | 12/1994 | Kreamer |
| 5,380,283 A | 1/1995 | Johnson |
| 5,387,226 A | 2/1995 | Miraki |
| 5,389,087 A | 2/1995 | Miraki |
| 5,395,335 A | 3/1995 | Jang |
| 5,397,302 A | 3/1995 | Weaver et al. |
| 5,409,459 A | 4/1995 | Gambale |
| 5,413,559 A | 5/1995 | Sirhan et al. |
| 5,415,639 A | 5/1995 | VandenEinde et al. |
| 5,448,993 A | 9/1995 | Lynch et al. |
| 5,449,363 A | 9/1995 | Brust et al. |
| 5,451,233 A | 9/1995 | Yock |
| 5,454,790 A | 10/1995 | Dubrul |
| 5,458,584 A | 10/1995 | Ginn et al. |
| 5,458,605 A | 10/1995 | Klemm |
| 5,460,168 A | 10/1995 | Masubuchi et al. |
| 5,462,530 A | 10/1995 | Jang |
| 5,480,389 A | 1/1996 | McWha et al. |
| 5,489,271 A | 2/1996 | Anderson |
| 5,490,837 A | 2/1996 | Blaeser et al. |
| 5,496,346 A | 3/1996 | Horzewski et al. |
| 5,501,227 A | 3/1996 | Yock |
| 5,531,700 A | 7/1996 | Moore et al. |
| 5,535,759 A | 7/1996 | Wilk |
| 5,536,234 A | 7/1996 | Newman |
| 5,536,248 A | 7/1996 | Weaver et al. |
| 5,540,236 A | 7/1996 | Ginn |
| 5,547,469 A | 8/1996 | Rowland et al. |
| 5,599,299 A | 2/1997 | Weaver et al. |
| 5,599,300 A | 2/1997 | Weaver et al. |
| 5,613,949 A | 3/1997 | Miraki |
| 5,626,600 A | 5/1997 | Horzewski et al. |
| 5,634,475 A | 6/1997 | Wolvek |
| 5,637,086 A | 6/1997 | Ferguson et al. |
| 5,685,853 A | 11/1997 | Bonnet |
| 5,693,015 A | 12/1997 | Walker et al. |
| 5,706,827 A | 1/1998 | Ehr et al. |
| 5,707,363 A | 1/1998 | Crawford et al. |
| 5,709,658 A | 1/1998 | Sirhan et al. |
| 5,718,680 A | 2/1998 | Kraus et al. |
| 5,725,504 A | 3/1998 | Collins |
| 5,765,682 A | 6/1998 | Bley |
| 5,788,681 A | 8/1998 | Weaver et al. |
| 5,800,414 A | 9/1998 | Cazal |
| 5,833,706 A | 11/1998 | St. Germain et al. |
| 5,836,306 A | 11/1998 | Duane et al. |
| 5,843,028 A | 12/1998 | Weaver et al. |
| 5,849,016 A | 12/1998 | Suhr |
| 5,851,189 A | 12/1998 | Forber |
| 5,899,850 A | 5/1999 | Ouchi |
| 5,921,971 A | 7/1999 | Agro et al. |
| 5,931,833 A | 8/1999 | Silverstein |
| 5,935,114 A | 8/1999 | Jang et al. |
| 5,978,699 A | 11/1999 | Fehse et al. |
| 6,007,522 A | 12/1999 | Agro et al. |

(56) References Cited

U.S. PATENT DOCUMENTS

| | | |
|---|---|---|
| 6,093,195 A | 7/2000 | Ouchi |
| 6,096,009 A | 8/2000 | Windheuser et al. |
| 6,106,487 A | 8/2000 | Duane et al. |
| 6,152,910 A | 11/2000 | Agro et al. |
| 6,190,333 B1 | 2/2001 | Valencia |
| 6,190,358 B1 | 2/2001 | Fitzmaurice et al. |
| 6,200,262 B1 | 3/2001 | Ouchi |
| 6,245,437 B1 | 6/2001 | Shiiki et al. |
| 6,277,100 B1 | 8/2001 | Raulerson et al. |
| 6,312,404 B1 | 11/2001 | Agro et al. |
| 6,322,577 B1 | 11/2001 | McInnes |
| 6,346,093 B1 | 2/2002 | Allman et al. |
| 6,371,944 B1 | 4/2002 | Liu et al. |
| 6,520,951 B1 | 2/2003 | Carrillo, Jr. et al. |
| 6,582,401 B1 | 6/2003 | Windheuser et al. |
| 6,606,515 B1 | 8/2003 | Windheuser et al. |
| 6,607,529 B1 | 8/2003 | Jones et al. |
| 6,663,597 B1 | 12/2003 | Windheuser et al. |
| 6,746,442 B2 | 6/2004 | Agro et al. |
| 6,746,466 B2 | 6/2004 | Eidenschink et al. |
| 6,764,484 B2 | 7/2004 | Richardson et al. |
| D498,992 S | 11/2004 | Bloom |
| 6,827,718 B2 | 12/2004 | Hutchins et al. |
| 6,851,424 B2 | 2/2005 | Scopton |
| 6,869,416 B2 | 3/2005 | Windheuser et al. |
| 6,879,854 B2 | 4/2005 | Windheuser et al. |
| 6,893,393 B2 | 5/2005 | Carrillo, Jr. |
| 6,925,323 B2 | 8/2005 | Snoke |
| 6,997,908 B2 | 2/2006 | Carrillo, Jr. et al. |
| 7,009,837 B2 | 3/2006 | Lo |
| 7,060,052 B2 | 6/2006 | Windheuser et al. |
| 7,076,285 B2 | 7/2006 | Windheuser et al. |
| 7,160,283 B2 | 1/2007 | Richardson et al. |
| 7,172,577 B2 | 2/2007 | Mangano et al. |
| 7,178,520 B2 | 2/2007 | Scopton |
| 7,179,252 B2 | 2/2007 | Agro et al. |
| 7,544,193 B2 | 6/2009 | Agro et al. |
| 2001/0020154 A1 | 9/2001 | Bigus et al. |
| 2001/0029362 A1 | 10/2001 | Sirhan et al. |
| 2001/0047135 A1 | 11/2001 | Daniels et al. |
| 2003/0088153 A1 | 5/2003 | Carrillo, Jr. et al. |
| 2003/0233043 A1 | 12/2003 | Windheuser et al. |
| 2004/0106852 A1 | 6/2004 | Windheuser et al. |
| 2004/0193142 A1 | 9/2004 | Agro et al. |
| 2005/0059890 A1 | 3/2005 | Deal et al. |
| 2005/0148950 A1 | 7/2005 | Windheuser et al. |
| 2005/0250983 A1 | 11/2005 | Tremaglio et al. |
| 2005/0288550 A1 | 12/2005 | Mathis |
| 2006/0229496 A1 | 10/2006 | Windheuser et al. |
| 2006/0247523 A1 | 11/2006 | Windheuser et al. |

FOREIGN PATENT DOCUMENTS

| | | |
|---|---|---|
| EP | 0388112 A2 | 9/1990 |
| EP | 0792657 A2 | 9/1997 |
| EP | 0801955 B1 | 3/1999 |
| JP | 50-108287 | 9/1975 |
| JP | 623055 A | 2/1994 |
| JP | 7155382 A | 6/1994 |
| WO | 9203963 | 3/1992 |
| WO | 9613296 | 5/1996 |
| WO | 9633764 | 10/1996 |
| WO | 9810820 | 3/1998 |
| WO | 9810821 | 3/1998 |
| WO | 9938557 | 8/1999 |
| WO | 9959664 | 11/1999 |
| WO | 0069499 | 11/2000 |
| WO | 0069500 | 11/2000 |
| WO | 2005107842 | 11/2005 |

OTHER PUBLICATIONS

Siegel, Jerome H., M.D. et al., "Two New Methods for Selective Bile Duct Cannulation and Sphincterotomy", Gastrointestinal Endoscopy, vol. 33, No. 6, Dec. 1987, pp. 438-440.

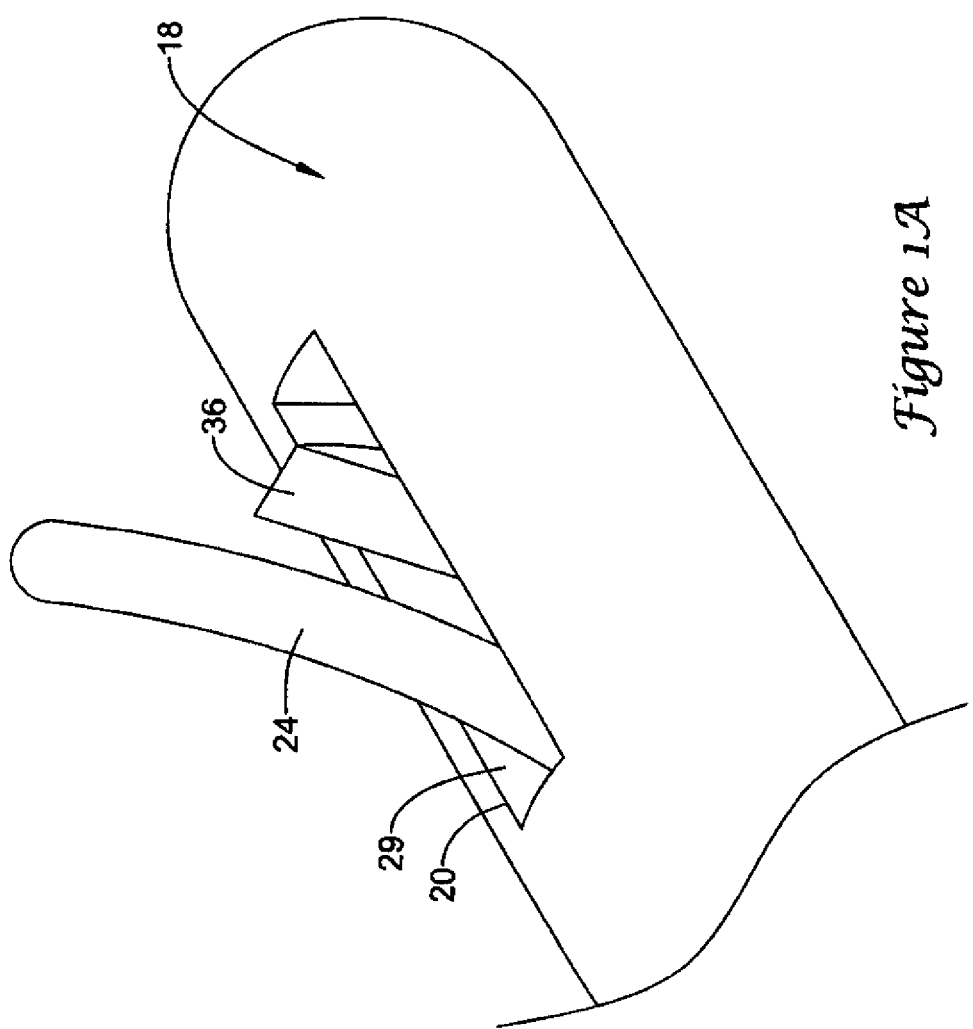

US 8,888,681 B2

METHOD AND APPARATUS FOR BILIARY ACCESS AND STONE RETRIEVAL

CROSS-REFERENCE TO RELATED APPLICATIONS

This application is a continuation of U.S. application Ser. No. 11/962,211, filed Dec. 21, 2007, now U.S. Pat. No. 8,372,000, which claims the benefit of Provisional U.S. Application No. 60/883,287 filed Jan. 3, 2007, the entire disclosures of which are incorporated herein by reference.

FIELD

The present invention relates to endoscopic medical devices and methods for making and using endoscopic medical devices. More particularly, the present invention relates to endoscopic devices that provide biliary and/or pancreatic access.

BACKGROUND

A wide variety of endoscopes, medical devices for use with endoscopes, and endoscopic procedures have been developed. Of the known endoscopes, medical devices for use with endoscopes, and endoscopic procedures, each has certain advantages and disadvantages. There is an ongoing need to provide alternative endoscopic devices as well as methods for making and using endoscopic devices.

SUMMARY

The disclosure provides design, material, and manufacturing method alternatives for endoscopes, medical devices for use with endoscopes, and for methods for making and using endoscopes and endoscopic devices. An example of a medical device for use with an endoscope is a catheter having a longitudinal slit, slot, or line of weakness formed therein. Some additional details regarding these and other embodiments are described in more detail below.

The above summary of some embodiments is not intended to describe each disclosed embodiment or every implementation of the present disclosure. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1A is a side view of a portion of the endoscopic instrument assembly shown in FIG. 1;

DETAILED DESCRIPTION

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
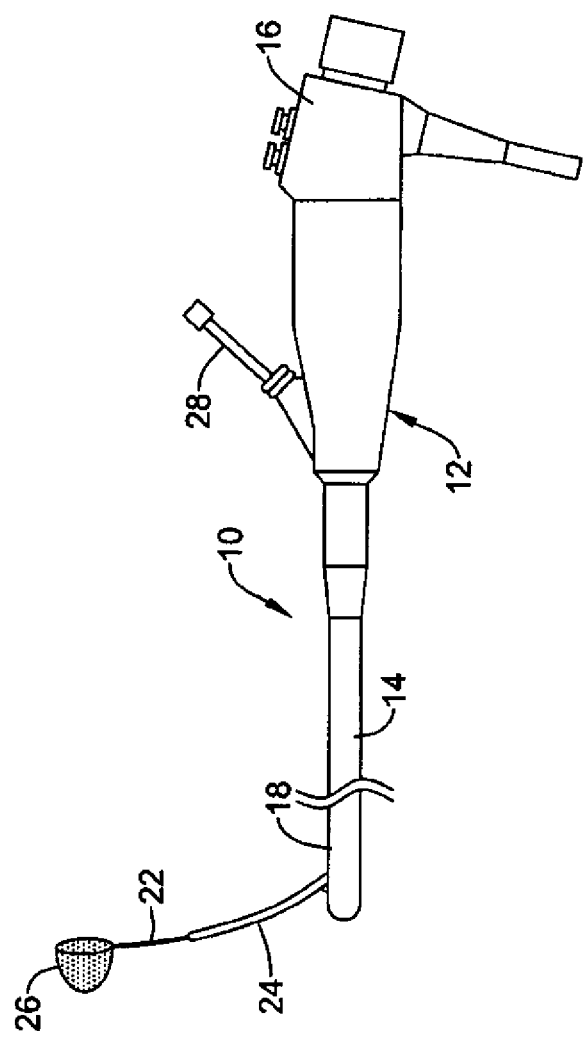
FIG. 1 is a side view of an illustrative endoscopic instrument assembly.

FIGS. 1 and 1A illustrate an example endoscopic instrument assembly 10. Assembly 10 includes an endoscope 12 having a shaft portion 14 and a handle portion 16. Shaft portion 14 includes a distal end region 18 and a distal port 20 where one or more medical devices (e.g., a guidewire or shaft 22 and/or a catheter 24) disposed within a working channel 29 formed in shaft portion 14 with medical devices are capable of extending out from. Shaft 22 may include an end effector 26 disposed at a distal end region thereof. An elevator 36 can be disposed adjacent port 20 that, when actuated, alters the angle at which catheter 24 (and/or shaft 22) exits port 20. Handle portion 16 includes one or more openings and/or a control region 28 where instruments (e.g., endoscopic instruments, guidewires, catheters, and the like) can gain access to working channel 29 and be extended through shaft portion 14 and out from port 20 or where fluids (e.g., contrast media, drugs, etc.) can be passed into a target site within a body lumen. Control region 28 may also include a control wire (not shown) for controlling elevator 36.

A vast number of endoscopic devices exist that have a wide variety of applications. At least some of these applications include advancing the endoscopic device along the biliary and/or pancreatic tract. When accessing the biliary and/or pancreatic tract, the position of the endoscopic device and/or the position of a particular medical device disposed in the endoscopic device may be important. This is because it may be challenging to precisely navigate the endoscope or endoscopic instrument through the anatomy of a patient. For example, when an endoscopic device is used for biliary applications, it may be difficult to advance the endoscopic device through the papilla of Vater and into the bile duct. Moreover, once a device is successfully advanced through the papilla of Vater, subtle movement of the device can result in the device being withdrawn back out from the papilla of Vater, necessitating another round of skilled maneuvering in order to proceed with the intervention.

When the endoscopic device is used to remove an object from a body lumen, for example a stone from the biliary tract, the potential for the endoscope and/or endoscopic device to lose its position can be further complicated. This is because stone removal may include advancing a stone removing device through a catheter disposed in the working channel of the endoscope and the withdrawing of the stone. Typically, it is the catheter that is precisely positioned and that maintains the position of the endoscopic instrument assembly, e.g., at or through the papilla of Vater. Because stones typically are too large to be retracted directly into the catheter itself, it is often necessary to remove the catheter along with the stone so that the stone can be passed from the biliary tract into the digestive tract, where it can be easily eliminated through natural or other interventional processes. This may cause the catheter and, ultimately, the endoscope to lose its desirable position in the biliary tract. A similar conundrum can be appreciated at other body lumens such as along the pancreatic tract.

Figure 2:
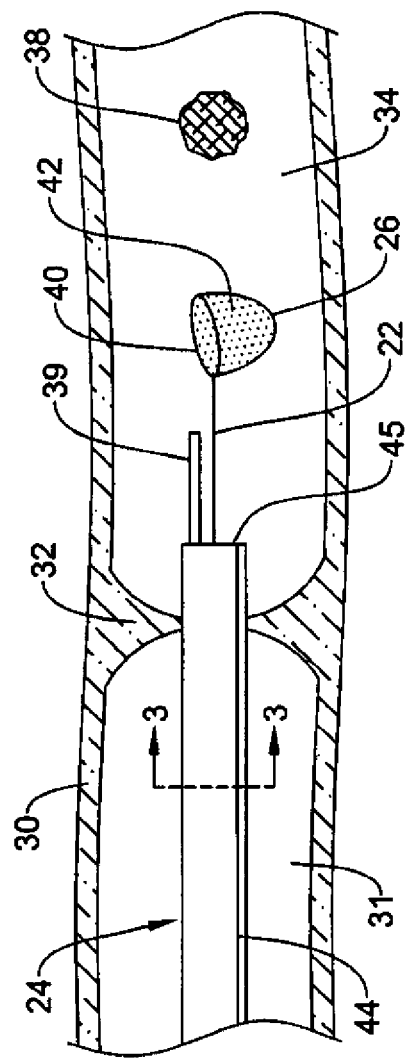
FIG. 2 is a partial cross-sectional side view of an illustrative endoscopic instrument disposed in a body lumen.

FIG. 2 depicts catheter 24 (that is configured to address at least some of the issues identified above) disposed in a body lumen 30. In some embodiments, body lumen 30 is adjacent the biliary tract 34. For example, catheter 24 may extend through the duodenum 31, pass through the papilla of Vater 32, and into the biliary tract 34 (e.g., adjacent the bile duct) to a position adjacent an object 38 (e.g., a stone) disposed in the biliary tract 34. In other embodiments, body lumen 30 may be along the pancreatic tract and adjacent the pancreatic duct. Of course, catheter 24 can likewise be positioned in any number of alternative body lumens 30 without departing from the spirit of the invention.

Shaft 22 is disposed in a lumen 46 (best seen in FIG. 3) formed in catheter 24. As mentioned above, shaft 22 may be provided with an end effector 26. End effector 26 may take a number of different forms. For example, end effector 26 may include a basket. The basket may have a loop or loop portion 40 and a basket portion 42. A number of alternative end effectors 26 are contemplated that may be utilized for a number of different interventions. Some of these alternative end effectors 26 may include loop portion 40 alone (i.e., without basket portion 42). Other end effectors 26 may include snares, needles, graspers, barbed graspers, forceps, hooks, laparoscopic instruments, arthroscopic instruments, cutting devices, lasers, and the like, or any other suitable device. In general, end effector 26 is configured to engage and/or remove object 38. In at least some embodiments, the shape, form, and/or configuration of end effector 26 is designed so that it is complementary to catheter 24. This may allow the combination of catheter 24 and end effector 26 to have a relatively low profile when catheter 24 is withdrawn, which may ease withdrawal of these devices.

To remove object 38 from body lumen 30, shaft 22 is advanced through lumen 46 to a position adjacent object 38. When positioned, end effector 26 can be engaged with object 38. In embodiments where end effector 26 is a loop or a basket, this may include capturing object 38 within end effector 26. Once engaged, shaft 22 can be proximally retracted so as to remove object 38 from the biliary tract 34.

In order for end effector 26 to be more easily engaged with stone 38, a secondary medical device 39 (e.g., a camera or optical device, grasper, holder, etc.) may be advanced through a secondary lumen 48 (best seen in FIG. 3) formed in catheter 24. In at least some embodiments, medical device 39 is an optical catheter that includes a visualization system capable of visualizing the target region within body lumen 30. Optical catheter 39 may extend proximally back to, for example, handle portion 16 of endoscope 12 where it may be connected to a suitable visualization monitor (not shown) so that a clinician may visualize the target region.

As described above, it may be desirable to hold or maintain the position of catheter 24 when it is positioned, for example, near or through the papilla of Vater 32. For the reasons set forth above, this may be complicated when catheter 24 is utilized to remove object 38, for example a stone, from body lumen 30. In order to improve the ability of catheter 24 (and/or endoscope 12) to hold its position, catheter 24 is provided with a longitudinal end effector passing region 44 that is formed therein.

End effector passing region 44 may take a number of different forms. For example, end effector passing region 44 may take the form of a slit formed through the wall of catheter 24 as depicted in FIG. 3. A slit is understood to be an opening that formed in the wall of catheter 24 such the cut ends are still in close proximity and/or contact with one another. End effector passing region 44 may extend along at least a portion of catheter 24 for any suitable distance. For example, end effector passing region 44 may extend from a distal end 45 of catheter 24 in the proximal direction about 1 centimeter to about 30 centimeters or more (including up to the full the length of catheter 24). In at least some embodiments, end effector passing region 44 extends a suitable length so that end effector 26 can be retracted therethrough from a position adjacent the biliary tract 34 to a position within the duodenum 31.

Figure 3A:
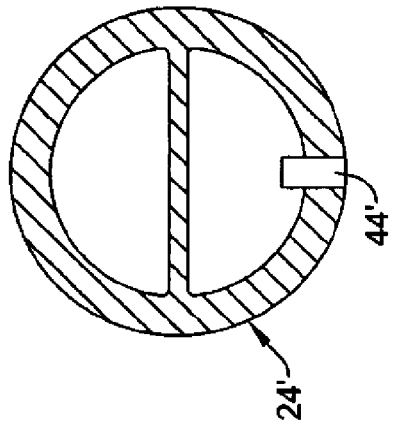
FIG. 3A is an alternative cross-sectional view depicting a slot.

Alternatively, end effector passing region 44 may comprise a slot formed in the wall of catheter 24' (that is otherwise the same in form and function as catheter 24) as depicted in FIG. 3A. A slot (marked in FIG. 3A by reference number 44') is understood to be a channel or opening formed in the wall of catheter 24'. The outward appearance of slot 44' is that portion of catheter where a piece of the wall is removed. Just like what is described above, slot 44' may extend from a distal end 45 of catheter 24' in the proximal direction about 1 centimeter to about 30 centimeters or more (including up to the full the length of catheter 24').

Figure 3C:
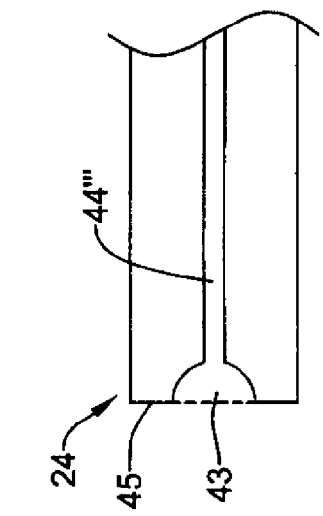
FIG. 3C is a bottom view of an alternative end effector passing region.
Figure 3:
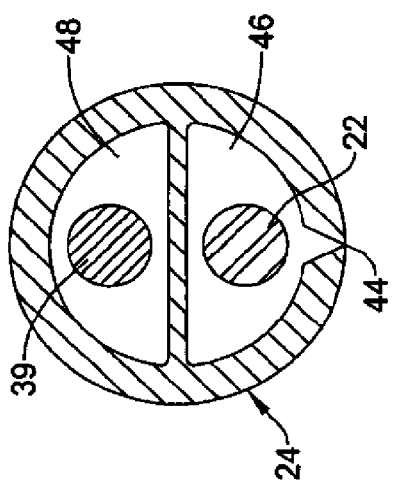
FIG. 3 is a cross-sectional view taken through line 3-3 of FIG. 2.
Figure 3B:
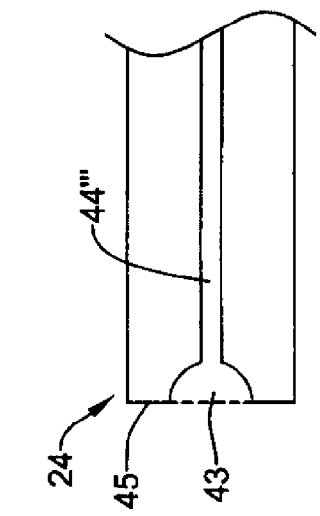
FIG. 3B is an alternative cross-sectional view depicting a horizontal line of weakness.

In still other embodiments, end effector passing region 44 may take the form of a horizontal line of weakness formed in catheter 24" (that is otherwise the same in form and function as catheters 24/24') as shown in FIG. 3B. A horizontal line of weakness (marked in FIG. 3B by reference number 44") is understood to be a closed perforation or other region where the wall of catheter 24" that is weakened, thereby allowing shaft 22 to relatively easily "tear through". Horizontal line of weakness 44" may be desirable, for example, because it allows contrast media to be infused through catheter 24" to the target region because the wall of catheter 24" remains essentially closed prior to being torn through. In some embodiments, horizontal line of weakness 44" can be created by placing a weaker polymeric material at the desired location for end effector passing region 44. Alternatively, horizontal line of weakness 44" may be defined by a mechanical mechanism or interlock (e.g., similar to the interlocking "zipper" on a ZIPLOC® or other zipper-type of bag), or any other suitable means. Just like what is described above, horizontal line of weakness 44" may extend from a distal end 45 of catheter 24" in the proximal direction about 1 centimeter to about 30 centimeters or more (including up to the full the length of catheter 24").

FIG. 3C illustrates that at least some embodiments of catheter 24 include an enlarged opening 43 adjacent to end effector passing region (marked generically in FIG. 3C by reference number 44'" to indicate that any of the previously-described end effector passing regions may include this feature). Enlarged opening 43 may function as a "funnel" or other type of directional guide that allows shaft 22 and/or end effector 26 to be more easily retracted therein in order to facilitate removal of catheter 24 and/or end effector 26. In at least some embodiments, opening 43 may include or be disposed adjacent an indentation or concave area of catheter 24 so as to further facilitate this "funneling" function. Opening 43 may be utilized in combination with any of the other end effector passing regions described herein. Indeed, any combination of slits 44, slots 44', and horizontal lines of weakness 44" can be used with or without opening 43 without departing from the spirit of the invention.

Figure 4:
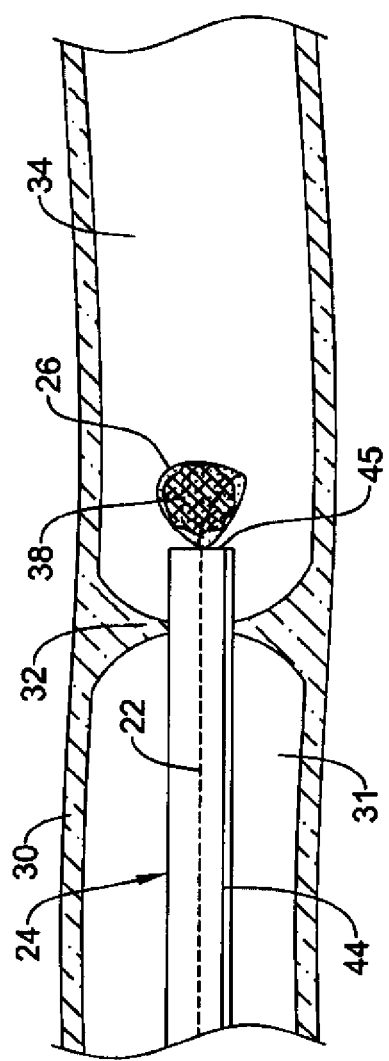
FIG. 4 is a partial cross-sectional side view of the endoscopic instrument shown in FIG. 2 that is engaged with an object within the body lumen.
Figure 5:
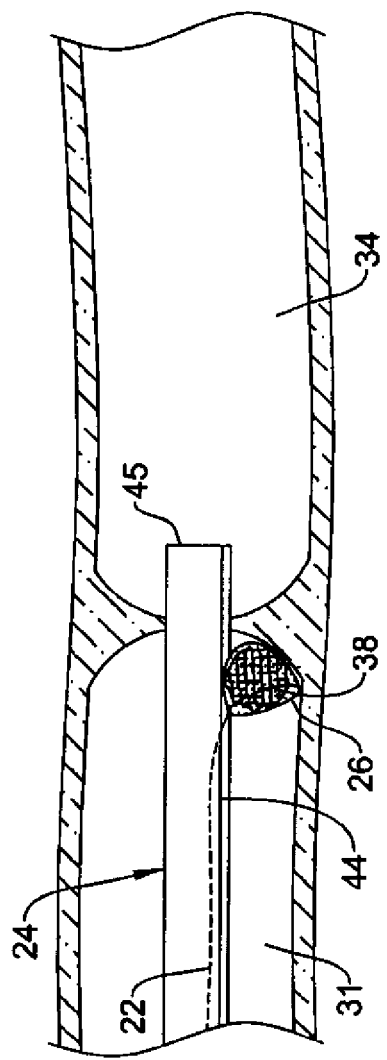
FIG. 5 is a partial cross-sectional side view of the endoscopic instrument shown in FIG. 2 where the object is proximally retracted.

Regardless of which form it takes, end effector passing region 44 allows shaft 22 to be retracted back along catheter 24 while end effector 26 is engaged with object 38. Turning now to FIG. 4, here it can be seen that with end effector 26 engaged with object 38, shaft 22 can be proximally retracted so that object 38 is adjacent to distal end region 45 of catheter 24. Because of the design of end effector passing region 44, shaft 22 may be further retracted as shown in FIG. 5. In doing so, end effector 26 (along with object 38) can follow end effector passing region 44 proximally. This may include end effector 26 being disposed along the outer wall of catheter 24 while being proximally retracted. This allows object 38 to be proximally retracted along catheter 24 from a position within the biliary tract 34, through the papilla of Vater 32, and into the duodenum 31 while the position of catheter 24 is maintained. Once in the duodenum 31, end effector 26 can be disengaged with object 38, thereby allowing object 38 to be passed through the digestive tract or otherwise removed.

Other than having end effector passing region 44, catheter 24 may be similar in form and function to a number of typical catheters that are suitable for use with an endoscope. For example, catheter 24 may be sized to fit within the working channel and have a length suitable to extend through the working channel and through the body lumen 30 to an area of interest. For example, catheter 24 may have an outside diameter of about 0.008 to about 0.50 inches. Lumens 46/48 may be sized to accommodate devices having an outside diameter of about 0.008 to about 0.50 inches.

In at least some embodiments, the materials chosen to construct catheter 24 contribute to at least some of the desirable properties of catheter 24. For example, catheter 24 may include metals, metal alloys, polymers, metal-polymer composites, and the like. Metals and metal alloys may desirably impact the pushability and/or the ability for catheter 24 to transmit torque. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY®ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., INS: R30003 such as ELGILOY®, PHYNOX®, and the like); platinum enriched stainless steel; combinations thereof; and the like; or any other suitable material. Depending on where along catheter 24 that the metal is used, some embodiments of catheter 24 include slits 44, slots 44', horizontal lines of weakness 44", and the like that are formed in metallic materials.

Polymeric materials may be utilized, for example, to improve the flexibility and/or reduce the trauma associated with interactions between catheter 24 and body lumen 30. Some examples of suitable polymers that may be used in the construction of catheter 24 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as to HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. Again, depending on where along catheter 24 that the metal is used, some embodiments of catheter 24 include slits 44, slots 44', horizontal lines of weakness 44", and the like that are formed in polymeric materials (and/or metal materials depending on the overall material composition of catheter 24).

In some embodiments, a coating, for example a lubricious, a hydrophilic, a protective, or other type of coating may be applied over portions or all of catheter 24, or other portions of assembly 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The sheath or polymeric layer may be formed, for example, by coating, by extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In at least some embodiments, catheter 24 may include a radiopaque marker band or coil (not shown). Such structures may be made from, doped with, or otherwise include a radiopaque material. Radiopaque materials are understood to be materials capable of producing a relatively bright image on a fluoroscopy screen or another imaging technique during a medical procedure. This relatively bright image aids the user of catheter 24 in determining its location. Some examples of radiopaque materials can include, but are not limited to, gold, platinum, molybdenum, palladium, tantalum, tungsten or tungsten alloy, plastic material loaded with a radiopaque filler, and the like. Depending on where along catheter 24 that the marker is used, some embodiments of catheter 24 include slits 44 that are formed in or extend through the marker.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for removing an object from a body lumen, the method comprising:
    advancing an elongate tubular member into a body lumen to a position adjacent a target region, the elongate tubular member having a distal end region, an end effector passing region formed along the distal end region, and a first lumen defined along at least partially a length thereof, and
    wherein an elongate shaft is slidably disposed in the first lumen, the elongate shaft having a distal end and an end effector disposed adjacent the distal end;
    advancing the elongate shaft out from the distal end region of the elongate tubular member so that the end effector is positioned distally of a distal end of the elongate tubular member adjacent an object disposed at the target region;
    engaging the object with the end effector; and
    retracting the elongate shaft including the end effector engaged with the object through the end effector passing region formed along the distal end region of the elongate tubular member so that the object is retracted to a position that is proximal of the distal end region of the elongate tubular member and adjacent an outer wall of the elongate tubular member.

2. The method of claim 1, wherein engaging the object with the end effector includes engaging a stone.

3. The method of claim 1, wherein retracting the elongate shaft so that the object is proximally retracted to a position that is proximal of the distal end region of the elongate tubular member includes disposing at least a portion of the end effector within the end effector passing region.

4. The method of claim 3, wherein the end effector passing region includes a horizontal line of weakness and wherein disposing at least a portion of the end effector within the end effector passing region includes tearing through the horizontal line of weakness.

5. The method of claim 3, wherein the end effector passing region includes a slit and wherein disposing at least a portion of the end effector within the end effector passing region includes passing through the slit.

6. The method of claim 1, wherein the elongate tubular member defines a second lumen, and further comprising advancing a medical device through the second lumen.

7. The method of claim 6, wherein advancing a medical device through the second lumen includes advancing an optical catheter through the second lumen.

8. The method of claim 7, further comprising visualizing the target region with the optical catheter.

9. A method for removing an object from a body lumen, the method comprising:
    advancing a tubular member into a body lumen to a position adjacent a target region;
    advancing an elongate shaft out from a distal end region of the tubular member so that an end effector of the elongate shaft is positioned distally of a distal end of the tubular member and positioned adjacent an object disposed at the target region;
    engaging the object with the end effector; and
    retracting the elongate shaft with respect to a distal end of the tubular member, including contacting a distally-facing opening in the distal end region of the tubular member while retracting the elongate shaft to dispose the end effector engaged with the object proximal the distal end of the tubular member such that the end effector extends through the tubular member and along an outer surface of the tubular member.

10. The method of claim 9, wherein engaging the object with the end effector includes engaging a stone.

11. The method of claim 9, wherein retracting the elongate shaft with respect to a distal end of the tubular member includes disposing at least a portion of the end effector within an end effector passing region of the distal end of the tubular member.

12. The method of claim 11, wherein the end effector passing region includes a horizontal line of weakness and wherein disposing at least a portion of the end effector within the end effector passing region includes tearing through the horizontal line of weakness.

13. The method of claim 11, wherein the end effector passing region includes a slot and wherein disposing at least a portion of the end effector within the end effector passing region includes passing through the slot.

14. The method of claim 9, wherein the tubular member defines a second lumen, and further comprising advancing a medical device through the second lumen.

15. The method of claim 14, further comprising:
    visualizing the target region, wherein the medical device includes an optical catheter.

16. A method of stone and/or tissue acquisition from a body lumen, the method comprising:
    advancing a catheter into a body lumen to a position adjacent a target region;
    advancing an elongate shaft through a lumen of the catheter to a position adjacent the target region;
    obtaining a stone and/or tissue by engaging an end effector of the elongate shaft with the stone and/or tissue at a position adjacent the target region, wherein the end effector is positioned distally of a distal end of the catheter; and
    retracting the end effector from the position adjacent the target region through an end effector passing region formed in the catheter to a position proximal a distal end of the catheter and adjacent an outer surface of the catheter.

17. The method of claim 16, wherein the step of retracting the end effector from the position adjacent the target region to a position proximal a distal end of the catheter and adjacent an outer surface of the catheter includes passing the end effector through an end effector passing region in the distal end of the catheter.

18. The method of claim 16, wherein the end effector includes a snare.

* * * * *